(12) United States Patent
Maw et al.

(10) Patent No.: US 7,053,122 B2
(45) Date of Patent: May 30, 2006

(54) THERAPEUTIC USE OF ARYL AMINO ACID DERIVATIVES

(75) Inventors: Graham Nigel Maw, Sandwich (GB); David James Rawson, Sandwich (GB); Lisa Rosemary Thompson, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/636,406

(22) Filed: Aug. 7, 2003

(65) Prior Publication Data

US 2004/0138197 A1    Jul. 15, 2004

Related U.S. Application Data

(60) Provisional application No. 60/409,526, filed on Sep. 9, 2002.

(30) Foreign Application Priority Data

Aug. 9, 2002    (GB) .................................. 0218590.8

(51) Int. Cl.
*A61K 31/135*    (2006.01)
*A61K 31/137*    (2006.01)
*A61K 31/13*    (2006.01)

(52) U.S. Cl. ...................... 514/649; 514/654; 424/319; 562/433

(58) Field of Classification Search ................ 562/433; 424/319; 514/649, 654
See application file for complete search history.

(56) References Cited

U.S. PATENT DOCUMENTS 4,024,175 A    5/1977    Satzinger et al.
4,087,554 A    5/1978    Haydock et al.

FOREIGN PATENT DOCUMENTS

WO    WO 95-31194    11/1995
WO    WO 95/31194 *    11/1995

OTHER PUBLICATIONS

Gee, N et al, "The Novel Anticonvusant Drug, Gabapentin (Neurontin), Binds to the Alpha. 2 Delta Subunit of a Calcium Channel", Journal of Biological Chemistry, Mar. 8, 1996, pp. 5768-5776, vol. 27, No. 10 Baltimore, MD, US.

* cited by examiner

*Primary Examiner*—Elvis O. Price
(74) *Attorney, Agent, or Firm*—Charles W. Ashbrook; David R. Kurlandsky

(57) ABSTRACT

The compounds of formula (I)

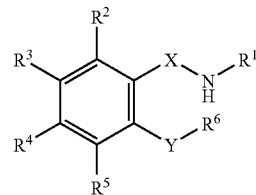

Formula (I)

are useful in the treatment of faintness attacks, hypokinesia, cranial disorders, neurodegenerative disorders, depression, anxiety, panic, neuropathic pain, neuropathological disorders and sleep disorders. Processes for the preparation of the final products and intermediates useful in the process are included. Pharmaceutical compositions containing one or more of the compounds are also included.

8 Claims, No Drawings

THERAPEUTIC USE OF ARYL AMINO ACID DERIVATIVES

This United States utility application claims the benefit of United Kingdom application number 0218590.8 filed Aug. 9, 2002 and U.S. Provisional application No. 60/409,526 filed Sep. 9, 2002.

This invention relates to novel aryl amino acid derivatives useful as pharmaceutical agents, to processes for their production, to pharmaceutical compositions containing them, and to their use for the treatment of the conditions set out below.

BACKGROUND TO THE INVENTION

Gabapentin (Neurontin®) is an anti-convulsant agent that is useful in the treatment of epilepsy and has recently been shown to be a potential treatment for neurogenic pain. It is 1-(aminomethyl)-cyclohexylacetic acid of structural formula:

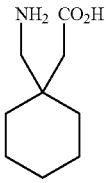

Gabapentin is one of a series of compounds of formula

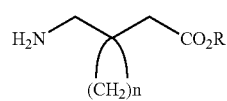

in which R is hydrogen or a lower alkyl radical and n is 4, 5, or 6. These compounds are described U.S. Pat. No. 4,024,175 and its divisional U.S. Pat. 4,087,544. Their disclosed uses are: protection against thiosemicarbazide-induced cramp; protection against cardiazole cramp; the cerebral diseases, epilepsy, faintness attacks, hypokinesia, and cranial traumas; and improvement in cerebral functions. The compounds are useful in geriatric patients. The disclosures of the above two patents are hereby incorporated by reference.

WO 95/31194, whose disclosure is incorporated by reference, discloses aminobenzoic acid derivatives and analogs of formula (A)

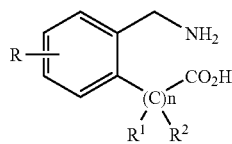

where n=0–10; R=H, OH, $C_{1-10}$ alkoxy, $C_{1-10}$ aminoalkyl, $SO_3H$, $C_{1-11}$ alkyl; $R^1$, $R^2$=H, OH, Me and their salts, esters, and amides, in combination with another medicament for the treatment of inflammation, useful for clinical treatment of chronic inflammatory diseases including arthritis, ileitis, and colitis and other inflammatory disorders, as well as trauma resulting from ischemia and subsequent reperfusion.

SUMMARY OF THE INVENTION

The present invention provides aryl amino acid derivatives and their prodrugs, and pharmaceutically acceptable salts and solvates useful in the treatment of a variety of disorders including faintness attacks, hypokinesia, cranial disorders, neurodegenerative disorders, depression, anxiety, panic, neuropathic pain, sleep disorders and neuropathological disorders. The compounds provided may also be useful in the treatment of premenstrual syndrome.

Thus, the invention provides the use of compounds of formula (I) or a pharmaceutically acceptable salt thereof in the manufacture of a medicament for the treatment of a disease selected from faintness attacks, hypokinesia, cranial disorders, neurodegenerative disorders, depression, anxiety, panic, neuropathic pain, sleep disorders and neuropathological disorders:

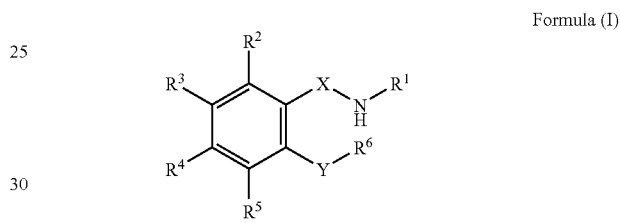

Formula (I)

wherein $R^1$ is H, $C_1$–$C_6$ alkyl or $C_3$–$C_8$ cycloalkyl;
X is —$(CH_2)_n$—$C(R^7)(R^8)$—;
Y is a direct link or —$(CH_2)_m$—$C(R^9)(R^{10})$—;
$R^7$, $R^8$, $R^9$ and $R^{10}$ are independently H or $C_1$–$C_6$ alkyl;
or $R^8$ and $R^1$ can be taken together with the nitrogen to which $R^1$ is attached to form a 4–8-membered heterocycloalkyl ring;
or $R^{10}$ and $R^1$ can be taken together with the nitrogen to which $R^1$ is attached to form a 4–8-membered heterocycloalkyl ring;
or $R^8$ and $R^{10}$ can be taken together with the carbons to which they are attached to form a 4–8-membered carbocyclic ring;
n is 0, 1 or 2;
m is 0, 1 or 2;
$R^2$, $R^3$, $R^4$ and $R^5$ are independently selected from H, $C_1$–$C_6$ alkyl, $C_1$–$C_6$ alkoxy, hydroxy, halogen, hydroxycarbonyl, $C_1$–$C_6$ alkoxycarbonyl, cyano, sulfonyl, $C_1$–$C_6$ alkylsulfonyl, thio, $C_1$–$C_6$ alkylthio, sulfonamide, perfluoro-$C_1$–$C_6$ alkyl, perfluoro-$C_1$–$C_6$ alkoxy, $C_3$–$C_8$ cycloalkyl, 4–8 membered heterocycloalkyl, amino, ($C_1$–$C_6$ alkyl or di-$C_1$–$C_6$ alkyl)amino, aminocarbonyl, ($C_1$–$C_6$ alkyl or di-$C_1$–$C_6$ alkyl)aminocarbonyl, $C_1$–$C_6$ acylamino, (N—$C_1$–$C_6$ alkyl)$C_1$–$C_6$ acylamino, phenyl or monocyclic heteroaryl, wherein phenyl and monocyclic heteroaryl are optionally substituted with $C_1$–$C_6$ alkyl, $C_1$–$C_6$ alkoxy, hydroxy, halogen, hydroxycarbonyl, $C_1$–$C_6$ alkoxycarbonyl or perfluoro-$C_1$–$C_6$ alkoxy;
or any one or two of $CR^2$, $CR^3$, $CR^4$ and $CR^5$ may be replaced with a nitrogen;
or $R^2$ and $R^3$ or $R^3$ and $R^4$ or $R^4$ and $R^5$ may be taken together with the carbons to which they are attached to form a fused $C_5$–$C_8$ cycloalkyl, 4–8 membered heterocycloalkyl, phenyl or monocyclic heteroaryl ring;

or $R^1$ and $R^2$ can be taken together with the nitrogen to which $R^1$ is attached to form a 4–8-membered heterocycloalkyl ring;

or $R^8$ and $R^2$ can be taken together with the carbons to which they are attached to form a 4–8-membered carbocyclic or heterocycloalkyl ring; and $R^6$ is hydroxycarbonyl or a carboxylic acid biostere or a prodrug thereof.

According to formula (I), $R^1$ is suitably H.

According to formula (I), Y is suitably a direct link.

According to formula (I), X is suitably —C($R^7$)($R^8$)—, or $R^7$ is suitably H and $R^8$ is suitably H or $C_1$–$C_6$ alkyl, e.g. methyl, or $R^8$ and $R^2$ suitably form a 4–8-membered carbocyclic ring, preferably a 5-membered carbocyclic ring, e.g. cyclopentyl, or $R^8$ and $R^1$ suitably form a 4–8-membered heterocycloalkyl ring, preferably a 5-membered heterocycloalkyl ring, e.g. a tetrahydropyran ring.

According to formula (I), $R^2$, $R^3$, $R^4$ and $R^5$ are suitably independently selected from H and halogen, e.g. bromide or chloride.

According to formula (I), $R^6$ is preferably hydroxycarbonyl, tetrazole or oxazolidinone, most preferably hydroxycarbonyl.

A preferred subgroup according to the present invention is represented by a compound of formula (II):

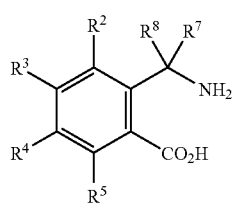

Formula (II)

wherein $R^7$ and $R^8$ are independently H or $C_1$–$C_6$ alkyl; and $R^2$, $R^3$, $R^4$ and $R^5$ are independently selected from H, $C_1$–$C_6$ alkyl, $C_1$–$C_6$ alkoxy, hydroxy, halogen, hydroxycarbonyl, $C_1$–$C_6$ alkoxycarbonyl, cyano, $C_1$–$C_6$ alkylsulfonyl, perfluoro-$C_1$–$C_6$ alkyl, perfluoro-$C_1$–$C_6$ alkoxy, $C_3$–$C_8$ cycloalkyl and 4–8 membered heterocycloalkyl;

or $R^8$ and $R^2$ can be taken together with the carbons to which they are attached to form a 4–8-membered carbocyclic or heterocycloalkyl ring.

Particularly preferred examples of the compounds of formula (I) are;

2-aminomethyl-5-chloro-benzoic acid;
2-aminomethyl-4,5-dichloro-benzoic acid;
2-aminomethyl-3-bromo-benzoic acid;
2-aminomethyl-6-chloro-benzoic acid;
2-(1-aminoethyl)-benzoic acid;
2,3-dihydro-1H-isoindole-4-carboxylic acid; and
3-(2-aminomethyl-5-chloro-phenyl)-4H-[1,2,4]oxadiazol-5-one;

or a pharmaceutically acceptable salt thereof.

It will be appreciated that certain compounds of formula (I) are novel and these compounds or a pharmaceutically acceptable salt, solvate, polymorph or pro-drug thereof form a further aspect of the present invention. The invention also relates to pharmaceutical compositions comprising the compounds and their use as a medicament.

In the above definitions, halo means fluoro, chloro, bromo or iodo. Alkyl and alkoxy, groups containing the requisite number of carbon atoms, except where indicated, can be unbranched- or branched-chain. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy.

4–8 membered heterocycloalkyl when used herein refers to a single saturated or partially unsaturated ring system containing at least one ring heteroatom independently selected from O, S and N. Suitable heterocycloalkyl groups include pyrrolidinyl, tetrahydrofuranyl, dihydrofuranyl, tetrahydropyranyl, pyranyl, thiopyranyl, aziridinyl, oxiranyl, methylenedioxyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, etc.

Monocyclic heteroaryl when used herein refers to a single aromatic ring containing at least one ring heteroatom independently selected from O, S and N. Suitable heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, etc.

$C_3$–$C_8$ cycloalkyl as used herein refers to a single saturated or partially unsaturated carbocyclic ring. Suitable cycloalkyl groups include cyclopropyl, cyclobutyl, cyclopentyl, cyclohexyl and cycloheptyl groups.

Carboxylic acid biostere when used herein refers to a group functionally equivalent to a carboxylic acid. Suitable biosteres include tetrazolyl, oxazolidinonyl, sulfonic acid, sulfinic acid, phosphonic acid, phosphinic acid, hydantoinyl, pyrrolidionyl and 3-isoxazolyl.

The present compounds can exist in unsolvated forms as well as solvated forms, including hydrated forms. In general, the solvated forms, including hydrated forms, which may contain isotopic substitutions (e.g. D2O, d6-acetone, d6-DMSO), are equivalent to unsolvated forms and are encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof. Separation of diastereoisomers or cis and trans isomers may be achieved by conventional techniques, e.g. by fractional crystallisation, chromatography or H.P.L.C. of a stereoisomeric mixture of a compound of the invention or a suitable salt or derivative thereof. An individual enantiomer of a compound of the invention may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The present invention also includes all suitable isotopic variations of a compound of the invention or a pharmaceutically acceptable salt thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that can be incorporated into compounds of the invention and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, 35S, $^{18}F$ and $^{36}Cl$, respectively. Certain isotopic variations of the compounds of the invention and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the compounds of the invention and pharmaceutically acceptable salts thereof of this invention can generally be prepared by conventional procedures such as by the illustrative methods or by the preparations described in the Examples and Preparations hereafter using appropriate isotopic variations of suitable reagents.

Since amino acids are amphoteric, pharmacologically compatible salts can be salts of appropriate non-toxic inorganic or organic acids or bases. Suitable acid addition salts are the hydrochloride/chloride, hydrobromide/bromide, hydroiodide/iodide, sulphate, bisulphate, nitrate, phosphate, hydrogen phosphate, acetate, fumarate, aspartate, besylate, bicarbonate/carbonate, camsylate, D and L-lactate, D and L-tartrate, edisylate, mesylate, malonate, orotate, gluceptate, methylsulphate, stearate, glucuronate, 2-napsylate, tosylate, hibenzate, nicotinate, isethionate, malate, maleate, citrate, gluconate, succinate, saccharate, benzoate, esylate, and pamoate salts. Suitable base salts are formed from bases which form non-toxic salts and examples are the sodium, potassium, aluminium, calcium, magnesium, zinc, choline, diolamine, olamine, arginine, glycine, tromethamine, benzathine, lysine, meglumine and diethylamine salts. Salts with quaternary ammonium ions can also be prepared with, for example, the tetramethyl-ammonium ion. The compounds of the invention may also be formed as a zwitterion.

A suitable salt of compounds of the present invention is the hydrochloride salt. For a review on suitable salts see Berge et al, J. Pharm. Sci., 66, 1–19, 1977.

Also included within the present scope of the compounds of the invention are polymorphs thereof.

Prodrugs of the above compounds are included in the scope of the instant invention. The effectiveness of an orally administered drug is dependent upon the drug's efficient transport across the mucosal epithelium and its stability in entero-hepatic circulation. Drugs that are effective after parenteral administration but less effective orally, or whose plasma half-life is considered too short, may be chemically modified into a prodrug form. A prodrug is a drug which has been chemically modified and may be biologically inactive at its site of action, but which may be degraded or modified by one or more enzymatic or other in vivo processes to the parent bioactive form. This chemically modified drug, or prodrug, should have a different pharmacokinetic profile to the parent, enabling easier absorption across the mucosal epithelium, better salt formulation and/or solubility, improved systemic stability (for an increase in plasma half-life, for example). These chemical modifications may be (1) Ester or amide derivatives which may be cleaved by, for example, esterases or lipases. For ester derivatives, the ester is derived from the carboxylic acid moiety of the drug molecule by known means. For amide derivatives, the amide may be derived from the carboxylic acid moiety or the amine moiety of the drug molecule by known means.

(2) Peptides which may be recognized by specific or nonspecific proteinases. A peptide may be coupled to the drug molecule via amide bond formation with the amine or carboxylic acid moiety of the drug molecule by known means.

(3) Derivatives that accumulate at a site of action through membrane selection of a prodrug form or modified prodrug form.

(4) Any combination of 1 to 3.

It will further be appreciated by those skilled in the art that certain moieties known to those skilled in the art as "promoieties", for example as described in "Design of Prodrugs" by H Bundgaard (Elsevier) 1985, may be placed on appropriate functionalities when such functionalities are present in compounds of the invention also to form a "prodrug". Further, certain compounds of the invention may act as prodrugs of other compounds of the invention. All protected derivatives, and prodrugs, of the compounds of the invention are included within the scope of the invention.

Research has shown that the oral absorption of certain drugs may be increased by the preparation of "soft" quaternary salts. The quaternary salt is termed a "soft" quaternary salt since, unlike normal quaternary salts, e.g., R—N$^+$(CH$_3$)$_3$, it can release the active drug on hydrolysis. "Soft" quaternary salts have useful physical properties compared with the basic drug or its salts. Water solubility may be increased compared with other salts, such as the hydrochloride, but more important there may be an increased absorption of the drug from the intestine. Increased absorption is probably due to the fact that the "soft" quaternary salt has surfactant properties and is capable of forming micelles and unionized ion pairs with bile acids, etc., which are able to penetrate the intestinal epithelium more effectively. The prodrug, after absorption, is rapidly hydrolyzed with release of the active parent drug.

Aminoacyl-glycolic and -lactic esters are known as prodrugs of amino acids (Wermuth C. G., *Chemistry and Industry*, 1980:433–435). The carbonyl group of the amino acids can be esterified by known means. Prodrugs and soft drugs are known in the art (Palomino E., *Drugs of the Future*, 1990; 15(4):361–368). The last two citations are hereby incorporated by reference.

The invention also relates to therapeutic use of the present compounds as agents for treating or relieving the symptoms of neurodegenerative disorders. Such neurodegenerative disorders include, for example, Huntington's disease, Parkinson's disease, and Amyotrophic Lateral Sclerosis. The present invention also covers treating neurodegenerative disorders termed acute brain injury. These include but are not limited to: head trauma, and asphyxia. Other incidents are head trauma, spinal cord trauma, or injury from general anoxia, hypoxia, hypoglycemia, hypotension as well as similar injuries seen during procedures from embole, hyperfusion, and hypoxia. The instant invention would be useful in a range of incidents, for example, during cardiac bypass surgery, in incidents of intracranial hemorrhage, in perinatal asphyxia and in cardiac arrest.

The compounds of the present invention are useful for the general treatment of pain, particularly neuropathic pain. Physiological pain is an important protective mechanism designed to warn of danger from potentially injurious stimuli from the external environment. The system operates through a specific set of primary sensory neurones and is exclusively activated by noxious stimuli via peripheral transducing mechanisms (Millan 1999 Prog. Neurobio. 57: 1–164 for an integrative Review). These sensory fibres are known as nociceptors and are characterised by small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred after complex processing in the dorsal horn, either directly or via brain stem relay nuclei to the ventrobasal thalamus and then on to the cortex, where the sensation of pain is generated.

Intense acute pain and chronic pain may involve the same pathways driven by pathophysiological processes and as such cease to provide a protective mechanism and instead contribute to debilitating symptoms associated with a wide range of disease states. Pain is a feature of many trauma and disease states. When a substantial injury, via disease or trauma, to body tissue occurs the characteristics of nociceptor activation are altered. There is sensitisation in the periphery, locally around the injury and centrally where the nociceptors terminate. This leads to hypersensitivity at the site of damage and in nearby normal tissue. In acute pain these mechanisms can be useful and allow for the repair processes to take place and the hypersensitivity returns to normal once the injury has healed. However, in many chronic pain states, the hypersensitivity far outlasts the healing process and is normally due to nervous system injury. This injury often leads to maladaptation of the afferent fibres (Woolf & Salter 2000 Science 288: 1765–1768). Clinical pain is present when discomfort and abnormal sensitivity feature among the patient's symptoms. Patients tend to be quite heterogeneous and may present with various pain symptoms. There are a number of typical pain subtypes: 1) spontaneous pain which may be dull, burning, or stabbing; 2) pain responses to noxious stimuli are exaggerated (hyperalgesia); 3) pain is produced by normally innocuous stimuli (allodynia) (Meyer et al., 1994 Textbook of Pain 13–44). Although patients with back pain, arthritis pain, CNS trauma, or neuropathic pain may have similar symptoms, the underlying mechanisms are different and, therefore, may require different treatment strategies. Therefore pain can be divided into a number of different areas because of differing pathophysiology, these include nociceptive, inflammatory, neuropathic pain etc. It should be noted that some types of pain have multiple aetiologies and thus can be classified in more than one area, e.g. Back pain, Cancer pain can have nociceptive inflammatory and neuropathic components.

Nociceptive pain is induced by tissue injury or by intense stimuli with the potential to cause injury. Pain afferents are activated by transduction of stimuli by nociceptors at the site of injury and sensitise the spinal cord at the level of their termination. This is then relayed up the spinal tracts to the brain where pain is perceived (Meyer et al., 1994 Textbook of Pain 13–44). The activation of nociceptors activates two types of afferent nerve fibres. Myelinated A-delta fibres transmitted rapidly and are responsible for the sharp and stabbing pain sensations, whilst unmyelinated C fibres transmit at a slower rate and convey the dull or aching pain. Moderate to severe acute nociceptive pain is a prominent feature of, but is not limited to pain from strains/sprains, post-operative pain (pain following any type of surgical procedure), posttraumatic pain, burns, myocardial infarction, acute pancreatitis, and renal colic. Also cancer related acute pain syndromes commonly due to therapeutic interactions such as chemotherapy toxicity, immunotherapy, hormonal therapy and radiotherapy. Moderate to severe acute nociceptive pain is a prominent feature of, but is not limited to, cancer pain which may be tumour related pain, (e.g. bone pain, headache and facial pain, viscera pain) or associated with cancer therapy (e.g. postchemotherapy syndromes, chronic postsurgical pain syndromes, post radiation syndromes), back pain which may be due to herniated or ruptured intervertebral discs or abnormalities of the lumber facet joints, sacroiliac joints, paraspinal muscles or the posterior longitudinal ligament Neuropathic pain is defined as pain initiated or caused by a primary lesion or dysfunction in the nervous system (IASP definition). Nerve damage can be caused by trauma and disease and thus the term 'neuropathic pain' encompasses many disorders with diverse aetiologies. These include but are not limited to, diabetic neuropathy, post herpetic neuralgia, back pain, cancer neuropathy, chemotherapy-induced neuropathy, HIV neuropathy, Phantom limb pain, Carpal Tunnel Syndrome, chronic alcoholism, hypothyroidism, trigeminal neuralgia, uremia, trauma-induced neuropathy, or vitamin deficiencies. Neuropathic pain is pathological as it has no protective role. It is often present well after the original cause has dissipated, commonly lasting for years, significantly decreasing a patients quality of life (Woolf and Mannion 1999 Lancet 353: 1959–1964). The symptoms of neuropathic pain are difficult to treat, as they are often heterogeneous even between patients with the same disease (Woolf & Decosterd 1999 Pain Supp. 6: S141–S147; Woolf and Mannion 1999 Lancet 353: 1959–1964). They include spontaneous pain, which can be continuous, or paroxysmal and abnormal evoked pain, such as hyperalgesia (increased sensitivity to a noxious stimulus) and allodynia (sensitivity to a normally innocuous stimulus).

The inflammatory process is a complex series of biochemical and cellular events activated in response to tissue injury or the presence of foreign substances, which result in swelling and pain (Levine and Taiwo 1994: Textbook of Pain 45–56). Arthritic pain makes up the majority of the inflammatory pain population. Rheumatoid disease is one of the commonest chronic inflammatory conditions in developed countries and rheumatoid arthritis (RA) is a common cause of disability. The exact aetiology of RA is unknown, but current hypotheses suggest that both genetic and microbiological factors may be important (Grennan & Jayson 1994 Textbook of Pain 397–407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder 2002 Ann Pharmacother. 36: 679–686; McCarthy et al., 1994 Textbook of Pain 387–395). Most patients with OA seek medical attention because of pain. Arthritis has a significant impact on psychosocial and physical function and is known to be the leading cause of disability in later life. Other types of inflammatory pain include but are not limited to inflammatory bowel diseases (IBD), Other types of pain include but are not limited to;

Musculo-skeletal disorders including but not limited to myalgia, fibromyalgia, spondylitis, sero-negative (non-rheumatoid) arthropathies, non-articular rheumatism, dystrophinopathy, Glycogenolysis, polymyositis, pyomyositis.

Central pain or 'thalamic pain' as defined by pain caused by lesion or dysfunction of the nervous system including but not limited to central post-stroke pain, multiple sclerosis, spinal cord injury, Parkinson's disease and epilepsy.

Heart and vascular pain including but not limited to angina, myocardial infarction, mitral stenosis, pericarditis, Raynaud's phenomenon, sclerodoma, skeletal muscle ischemia.

Visceral pain, and gastrointestinal disorders. The viscera encompasses the organs of the abdominal cavity. These organs include the sex organs, spleen and part of the digestive system. Pain associated with the viscera may be neuropathic, nociceptive as well as inflammatory and can be divided into digestive visceral pain and non-digestive visceral pain. Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (IBS) and functional abdominal pain syndrome (FAPS), and—for IBD, Crohn's disease, ileitis, and ulcerative colitis, which all regularly produce visceral pain. Other types of visceral pain include the pain associated with dysmenorrhea, pelvic pain, cystitis and pancreatitis.

Few drugs are known to act selectively upon GI disorder-associated hypersensitivity (Farthing M. J. (1998) Drugs 56:11–21). Available treatments of pain fall into two main categories: (1) nonsteroidal anti-inflammatory drugs, used to treat mild pain, but whose therapeutic use is limited by GI adverse effects (gastric erosion, peptide ulcer formation, inflammation of the duodenum and colon); (2) morphine and related opioids, used to treat moderate to severe pain but whose therapeutic use is limited by undesirable side effects including constipation, respiratory depression, tolerance and abuse potential.

Head pain including but not limited to migraine, migraine with aura, migraine without aura, cluster headache, tension-type headache.

Orofacial pain including but not limited to dental pain, temporomandibular myofascial pain.

The compounds of formula (I) are preferably used for the treatment of neuropathic pain.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM.

As a alternative aspect of the invention, there is provided a method for treating a disease selected from faintness attacks, hypokinesia, cranial disorders, neurodegenerative disorders, depression, anxiety, panic, neuropathic pain, sleep disorders, and neuropathological disorders, comprising administering a therapeutically effective amount of a compound of formula (I) to a mammal in need of said treatment.

The biological activity of the compounds of the invention may be measured in a radioligand binding assay using [$^3$H]gabapentin and the $\alpha_2\delta$ subunit derived from porcine brain tissue (Gee N. S., Brown J. P., Dissanayake V. U. K., Offord J., Thurlow R., Woodruff G. N., J. Biol. Chem., 1996; 271:5776–5879). Results may be expressed in terms of µM or nM $\alpha_2\delta$ binding affinity.

The compounds of the instant invention may be administered in combination, either separately, simultaneously or sequentially, with one or more other pharmacologically active agents. Suitable agents, particularly for the treatment of neuropathic pain, include:

(i) opioid analgesics, e.g. morphine, heroin, hydromorphone, oxymorphone, levorphanol, levallorphan, methadone, meperidine, tentanyl, cocaine, codeine, dihydrocodeine, oxycodone, hydrocodone, propoxyphene, nalmefene, nalorphine, naloxone, naltrexone, buprenorphine, butorphanol, nalbuphine and pentazocine;

(ii) nonsteroidal antiinflammatory drugs (NSAIDs), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and their pharmaceutically acceptable salts;

(iii) barbiturate sedatives, e.g. amobarbital, aprobarbital, butabarbital, butabital, mephobarbital, metharbital, methohexital, pentobarbital, phenobartital, secobarbital, talbutal, theamylal, thiopental and their pharmaceutically acceptable salts;

(iv) benzodiazepines having a sedative action, e.g. chlordiazepoxide, clorazepate, diazepam, flurazepam, lorazepam, oxazepam, temazepam, triazolam and their pharmaceutically acceptable salts, (v) $H_1$ antagonists having a sedative action, e.g. diphenhydramine, pyrilamine, promethazine, chlorpheniramine, chlorcyclizine and their pharmaceutically acceptable salts;

(vi) miscellaneous sedatives such as glutethimide, meprobamate, methaqualone, dichloralphenazone and their pharmaceutically acceptable salts; skeletal muscle relaxants, e.g. baclofen, carisoprodol, chlorzoxazone, cyclobenzaprine, methocarbamol, orphrenadine and their pharmaceutically acceptable salts, (vii) NMDA receptor antagonists, e.g. dextromethorphan ((+)-3-hydroxy-N-methylmorphinan) and its metabolite dextrorphan ((+)-3-hydroxy-N-methylmorphinan), ketamine, memantine, pyrroloquinoline quinone and cis-4-(phosphonomethyl)-2-piperidinecarboxylic acid and their pharmaceutically acceptable salts;

(viii) alpha-adrenergic active compounds, e.g. doxazosin, tamsulosin, clonidine and 4-amino-6,7-dimethoxy-2-(5-methanesulfonamido-1,2,3,4-tetrahydroisoquinol-2-yl)-5-(2-pyridyl)quinazoline;

(ix) tricyclic antidepressants, e.g. desipramine, imipramine, amytriptiline and nortriptiline;

(x) anticonvulsants, e.g. carbamazepine, gabapentin, pregabalin and valproate;

(xi) serotonin reuptake inhibitors, e.g. fluoxetine, paroxetine, citalopram and sertraline;

(xii) mixed serotonin-noradrenaline reuptake inhibitors, e.g. milnacipran, venlafaxine and duloxetine; noradrenaline reuptake inhibitors, e.g. reboxetine;

(xiii) Tachykinin (NK) antagonists, particularly Nk-3, NK-2 and NK-1 e.g. antagonists, ($\alpha$R,9R)-7-[3,5-bis(trifluoromethyl)benzyl]-8,9,10,11-tetrahydro-9-methyl-5-(4-methylphenyl)-7H-[1,4]diazocino[2,1 g][1,7]naphthridine-6-13-dione(TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine(2S,3S)

(xiv) Muscarinic antagonists, e.g oxybutin, tolterodine, propiverine, tropsium chloride and darifenacin;

(xv) PDEV inhibitors such as sildenafil, vardenafil and Cialis (Trade Mark);

(xvi) COX-2 inhibitors, e.g. celecoxib, rofecoxib and valdecoxib;

(xvii) Non-selective COX inhibitors (preferably with GI protection), e.g. nitroflurbiprofen (HCT-1026);

(xviii) coal-tar analgesics, in particular, paracetamol;

(xix) neuroleptics, such as droperidol;

(xx) Vanilloid receptor agonists, e.g. resinferatoxin;

(xxi) Beta-adrenergic compounds such as propranolol;

(xxii) Local anaesthetics, such as mexiletine;

(xxiii) Corticosteriods, such as dexamethasone (xxiv) serotonin receptor agonists and antagonists; cholinergic (nicotinic) analgesics; and (xxv) miscellaneous agents such as Tramadol®.

Combinations of the compounds of the present invention and other therapeutic agents may be administered separately, sequentially or simultaneously. Thus, the present invention extends to a kit comprising a compound of formula (I), one or more other therapeutic agents, such as those listed above, and a suitable container.

The compounds of the invention can be administered alone or in combination with other drugs but will generally be administered in an admixture with suitable pharmaceutical excipient(s), diluent(s) or carrier selected with regard to the intended route of administration and standard pharmaceutical practice. The term "excipient" is used herein to describe any ingredient other than the compound of the invention. If appropriate, auxiliaries can be added. Auxiliaries are preservatives, anti-oxidants, flavours or colourants. The compounds of the invention may be administered in a composition of the immediate-, delayed-, modified-, sustained-, pulsed- or controlled-release type.

The compounds of formula (I) can be administered, for example but not limited to the following routes: orally, buccally or sublingually in the form of tablets, capsules, multi- and nano-particulates, liquids, gels, films (incl. mucoadhesive), powders, ovules, elixers, lozenges (incl. liquid-filled), chews, solutions, suspensions and sprays. The compounds of formulae (I) may also be administered as osmotic dosage form, or in the form of a high energy dispersion or as coated particles or fast-dissolving, fast-disintegrating dosage form such as those described in Expert Opinion in Therapeutic Patents, 11(6), 981–986 by Liang and Chen (2001). The compounds of the formula (I) may be administered as crystalline or amorphous products. They may be obtained, for example as solid plugs, powders or films, by methods such as precipitation, crystallization, freeze drying, spray drying or evaporative drying. Microwave or radio frequency drying may also be used for this purpose. Suitable formulations of the compounds of formula (I) may be in hydrophilic or hydrophobic matrix, ion-exchange resin complex, coated or uncoated form and other types as described in U.S. Pat. No. 6,106,864 as desired. Such pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), mannitol, disintegrants such as sodium starch glycolate, crosscarmellose sodium and certain complex silicates, and granulation binders such as polyvinylpyrrolidone, hydroxypropylmethylcellulose (HPMC), triglycerides, hydroxypropylcellulose (HPC), bentonite sucrose, sorbitol, gelatin and acacia. Additionally, lubricating agents may be added to solid compositions, for example magnesium stearate, stearic acid, glyceryl behenate, PEG and talc or wetting agents, such as sodium lauryl sulphate or preservatives, anti-oxidants, flavours and colourants. Additionally, polymers such as carbohydrates, phospholipids and proteins may be included.

Fast dispersing or dissolving dosage formulations (FD-DFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol or xylitol. The terms dispersing or dissolving as used herein to describe FDDFs are dependent upon the solubility of the drug substance used, i.e. where the drug substance is insoluble a fast dispersing dosage form can be prepared and where the drug substance is soluble a fast dissolving dosage form can be prepared.

The solid dosage forms, such as tablets are manufactured using standard processes known to a forumaltionchemist, for example, by direct compression, wet, dry or melt granulation, melt congealing or extrusion. The tablet cores which may be mono or multi-layer may be coated with appropriate overcoats known in the art.

Solid formulations for oral administration may be formulated to be immediate and/or modified release. Modified release formulations include delayed-, sustained-, pulsed-, controlled-, targeted and programmed release. Suitable modified release formulations for the purposes of the invention are described in U.S. Pat. No. 6,106,864. Details of other suitable release technologies such as high energy dispersions and osmotic and coated particles are to be found in Verma et al., Pharmaceutical Technology On-line, 25(2), 1–14 (2001).

Solid compositions of a similar type may also be employed as fillers in capsules such as gelatin, starch or HPMC capsules. Preferred excipients in this regard include lactose, starch, a cellulose, milk sugar or high molecular weight polyethylene glycols. Liquid compositions may be employed as fillers in soft or hard capsules, such as gelatin capsule, and typically comprise a carrier, for example water, ethanol, propylene glycol, methylcellulose or a suitable oil, and one or more emulsifying agents and/or suspending agents. For aqueous and oily suspensions, solutions, syrups and/or elixirs, the compounds of the invention may be combined with various sweetening or flavouring agents, colouring matter or dyes, with emulsifying and/or suspending agents and with diluents such as water, ethanol, propylene glycol, methylcellulose, alginic acid or sodium alginate, glycerin, oils, hydrocolloid agents and combinations thereof. Moreover, formulations containing these compounds and excipients may be presented as a dry product for reconstitution with water or other suitable vehicles before use.

Liquid form preparations include solutions, suspensions, syrups, elixirs and emulsions, for example, water or water propylene glycol solutions. For parenteral injection liquid preparations can be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

The compounds of the present invention can also be administered by injection, that is, intravenously, intramuscularly, intracutaneously, intraduodenally, or intraperitoneally, intra-arterially, intrathecally, intraventricularly, intraurethrally, intrasternally, intracranially, intraspinally or subcutaneously. Suitable devices for parenteral administration include needle (including microneedle) injectors, needle-free injectors, infusion or implant injection techniques. For such parenteral administration they are best used in the form of a sterile aqueous solution, suspension or emulsion (or system so that can include micelles) which may contain other substances known in the art, for example, enough salts or carbohydrates, such as glucose to make the solution isotonic with blood. The aqueous solutions should be suitably buffered (preferably to a pH of from 3 to 9), if necessary. For some forms of parenteral administration they may be used in the form of a sterile non-aqueous system such as fixed oils, including mono- or diglycerides, and fatty acids, including oleic acid. The preparation of suitable parenteral formulations under sterile conditions for example lyophilisation is readily accomplished by standard pharmaceutical techniques well-known to those skilled in the art. Alternatively, the active ingredient may be in a dried form to be used in conjunction with a suitable vehicle such as sterile, pyrogen-free water.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Thus, compounds of formula (I) may be formulated in a more solid form for administration as an implanted depot providing long-term release of the active compound.

Also, the compounds of the present invention can be administered intranasally or by inhalation. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomiser (preferably an atomiser using electrohydrodynamics to produce a fine mist) or nebuliser, with or without the use of a suitable propellant, e.g. dichlorodifluoromethane, trichlorofluoromethane, dichlorotetrafluoroethane, a hydrofluoroalkane such as 1,1,1,2-tetralfuoroethane (HFA 134A [trade mark]) or 1,1,1,2,3,3,3-heptafluoropropane (HFA 227EA [trade mark]), carbon dioxide, a further perfluorinated hydrocarbon such as Perflubron [trade mark] or other suitable gas.

The pressurised container, pump, spray, atomiser or nebuliser may contain a solution or suspension of the active compound, for example using a mixture of ethanol (optionally, aqueous ethanol) or a suitable agent for dispersing, solubilising or extending release and the propellant as the solvent, which may additionally contain a surfactant, such as sorbitan trioleate or an oligolactic acid. Capsules, blisters and cartridges (made, for example from gelatin or HPMC) for use in an inhaler or insufflator may be formulated to contain a powder mix of the compound of the invention, a suitable powder base such as lactose or starch and a performance modifier such as I-leucine, mannitol or magnesium stearate.

In the case of dry powder inhalers and aerosols, the dosage unit is determined by means of a valve which delivers a metered amount.

Prior to use in a dry powder formulation or suspension formulation for inhalation the compound of the invention is micronised to a size suitable for delivery by inhalation (typically considered as less than 5 microns). Micronisation may be achieved by any appropriate comminuting method, for example spiral jet milling, fluid bed jet milling, supercritical fluid processing to form nanoparticles, high pressure homogenisation or by spray drying.

A suitable solution formulation for use in an atomiser using electrohydrodynamics to produce a fine mist may contain from 1 µg to 10 mg of the compound of the invention per actuation and the actuation volume may vary from 1 µl to 100 µl. A typical formulation may comprise a compound of formula (I), propylene glycol, sterile water, ethanol and sodium chloride. Alternative solvents may be used in place of propylene glycol, for example glycerol or polyethylene glycol.

Formulations for inhaled/intranasal administration may be formulated to be immediate and/or modified release.

Alternatively, the compounds of the invention may be administered topically to the skin or mucosa, either dermally or transdermally, for example, in the form of a gel, hydrogel, lotion, solution, cream, ointment, dusting powder, dressing, foam, film, skin patch, wafers, implant, sponges, fibres, bandage, microemulsion and combinations thereof. Liposomes may also be used. For such applications, the compounds formula (I) can be suspended or dissolved in, for example, a mixture with one or more of the following: mineral oil, liquid petrolatum, white petrolatum, glycerin, propylene glycol, polyoxyethylene polyoxypropylene compound, emulsifying wax, fixed oils, including synthetic mono- or diglycerides, and fatty acids, including oleic acid, water, sorbitan monostearate, a polyethylene glycol, liquid paraffin, polysorbate 60, cetyl esters wax, cetearyl alcohol, 2-octyldodecanol, benzyl alcohol, alcohols such as ethanol. Alternatively, penetration enhancers may be used—see, for example J. Pharm. Sci., 88(10), 955–958 by Finnin and Morgan (October 1999). The following may also be used polymers, carbohydrates, proteins, phospholipids in the form of nanoparticles (such as niosomes or liposomes) or suspended or dissolved. In addition, they may be delivered using iontophoresis, electroporation, phonophoresis and sonophoresis.

Other means of topical administration include delivery by iontophoresis, electroporation, phonophoresis, sonophoresis and needle-free or microneedle injection.

Formulations for topical administration may be formulated to be immediate and/or modified release.

Alternatively, the compounds of the invention can be administered rectally, for example in the form of a suppository, pessary or enema. They may also be administered by vaginal route. For example, but not limited to the following presentations, these compositions may be prepared by mixing the drug with a suitable non-irritant excipients, such as cocoa butter, synthetic glyceride esters or polyethylene glycols, which are solid at ordinary temperatures, but liquefy and/or dissolve in the cavity to release the drug.

Formulations for rectal/vaginal administration may be formulated to be immediate and/or modified release.

The compounds of the invention may also be administered directly to the eye or ear. For ocular and aural administration, the compounds of formula (I) can be formulated as micronised suspensions or solutions in isotonic, pH adjusted, sterile saline. A polymer may be added such as crossed-linked polyacrylic acid, polyvinylalcohol, hyaluronic acid, a cellulosic polymer (e.g. hydroxypropylmethylcellulose, hydroxyethylcellulose or methyl cellulose), or a heteropolysaccharide polymer (e.g. gelan gum). Alternatively, they may be formulated in an ointment such as petrolatum or mineral oil, incorporated into bio-degradable (e.g. absorbable gel sponges, collagen) or non-biodegradable (e.g. silicone) implants, wafers, drops, lenses or delivered via particulate or vesicular systems such as niosomes or liposomes. Formulations may be optionally combined with a preservative, such as benzalkonium chloride. In addition, they may be delivered using iontophoresis. Formulations for ocular/aural administration may be formulated to be immediate and/or modified release.

The compounds of the invention may also be used in combination with soluble macromolecular entities such as cyclodextrin or polyethylene glycol-containing polymers to improve their solubility, dissolution rate, taste-masking, bioavailability and/or stability. Drug-cyclodextrin complexes are generally useful for most dosage forms and administration routes. Both inclusion and non-inclusion complexes may be used. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

The term 'administered' includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, lipsomes, immunoliposomes, lipofectin, cationic facial amphiphiles (CFAs) and combinations thereof. The routes for such delivery mechanisms include but are not limited to mucosal, nasal, oral, parenteral, gastrointestinal, topical or sublingual routes.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1 g according to the particular application and the potency of the active component. In medical use the drug may be administered three times daily as, for example, capsules of 100 or 300 mg. In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The pharmaceutical composition according to the present invention can, if desired, also contain one or more other compatible therapeutic agents. In particular, the composition can be combined with any one or more compounds useful in the treatment of pain, such as those listed above. Thus, the present invention presents a pharmaceutical composition comprising a compound of formula (I) or (II) one or more other pharmacologically active agents and one or more pharmaceutically acceptable carriers.

It is to be appreciated that all references herein to treatment include curative, palliative and prophylactic treatment.

GENERAL METHODS

According to a first process A, where Y is a direct link, $R^1$ is H and $R^6$ is $CO_2H$, a compound of formula (I) may be prepared by ring opening of a lactam of formula (III);

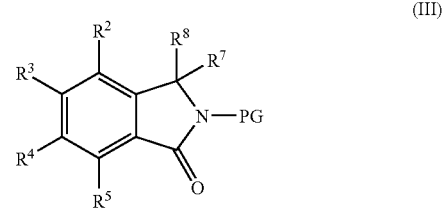

where PG is H or a suitable protecting group, such as tert-butoxycarbonyl, by acid hydrolysis using a suitable acid such as hydrochloric acid in a suitable solvent such as dioxan or by base mediated ring opening using a hydroxide source, such as lithium hydroxide, in a suitable solvent such as tetrahydrofuran, followed by deprotection of any protecting group present by methods known in the art, for example treatment with an acid such as hydrochloric acid in a suitable solvent such as diethyl ether or dioxan.

According to a second process B, where Y is a direct link and $R^1$ is H, a compound of formula (I) may be prepared by deprotection of a compound of formula (IV) by methods known in the art;

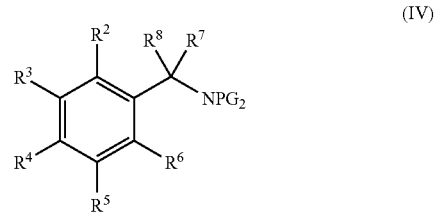

where PG is a suitable protecting group. Typically, where PG is tert-butoxycarbonyl, deprotection may be carried out by treatment with an acid such as hydrochloric acid in a suitable solvent such as diethyl ether or dioxan.

According to a third and fourth process C and D, where $R^1$ is H, Y is a direct link, $R^2$, $R^3$, $R^4$ and $R^5$ are not cyano, thio or amino and $R^6$ is tetrazole or an oxazolidinone, a compound of formula (IV) may be prepared from a compound of formula (V) according to Scheme 1.

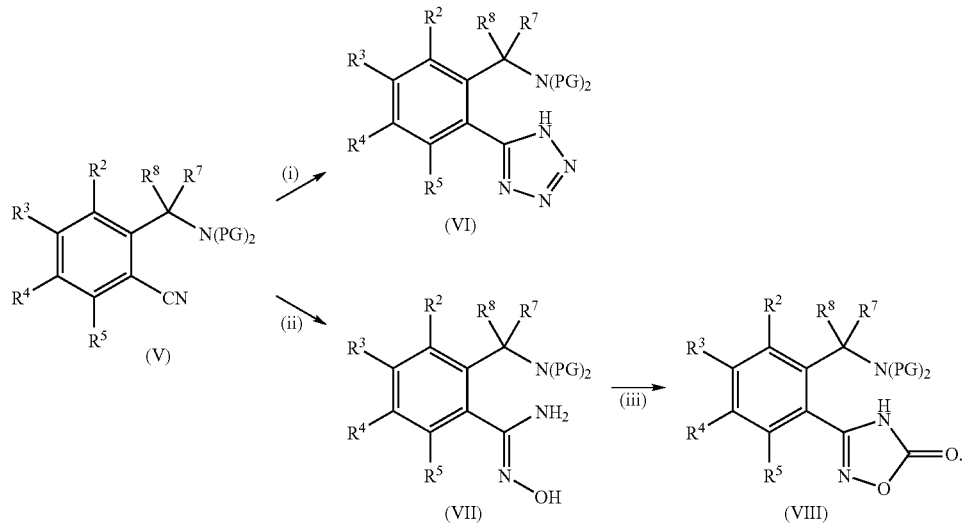

Scheme 1

Typical reaction conditions;

(i) Treatment of (V) with a suitable azide source such as sodium azide with NH$_4$Cl or trimethylsilyl azide in a suitable solvent such as DMF at reflux.

(ii) Treatment of (V) with a suitable hydroxylamine source such as hydroxylamine hydrochloride and an acid acceptor such as triethylamine in a suitable solvent such as absolute ethanol at elevated temperatures.

(iii) Treatment of (VII) with a suitable carbonyl source such as carbonyl dimimidazole in a suitable solvent such as tetrahydrofuran at elevated temperatures.

According to a fifth process E, where $R^1$ is H, $R^2$ and $R^8$ form a 5-membered carbocyclic ring, $R^3$, $R^4$ and $R^5$ are not cyano, thio or amino and Y is a direct link, a compound of formula (I) may be prepared from a compound of formula (IX) according to Scheme 2.

Typical reaction conditions.

(i) Treatment of (IX) with a suitable hydroxylamine source such as hydroxylamine hydrochloride and an acid acceptor such as triethylamine in a suitable solvent such as methanol or ethanol at room temperature.

(ii) Reduction of (X) using a suitable proton source such as glacial acetic acid or hydrochloric acid and sodium amalgam, zinc or hydrogen with catalytic palladium in a suitable solvent such as methanol at elevated temperatures.

According to a sixth process F, where $R^1$ and $R^2$ form a 5-membered carbocyclic ring, $R^3$, $R^4$ and $R^5$ are not cyano, thio or amino and Y is a direct link, a compound of formula (I) may be prepared from a compound of formula (XI) according to Scheme 3.

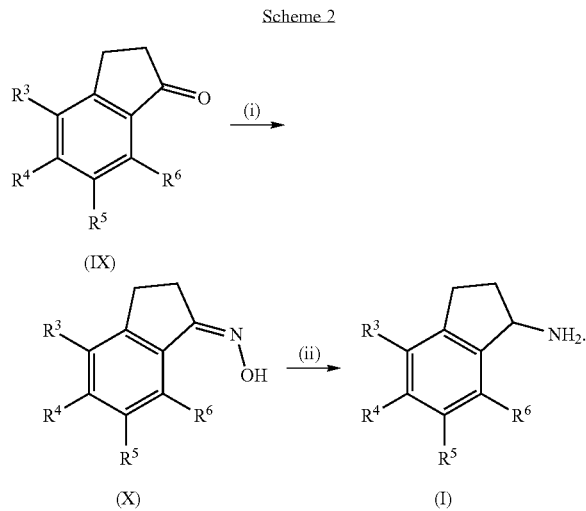

Scheme 2

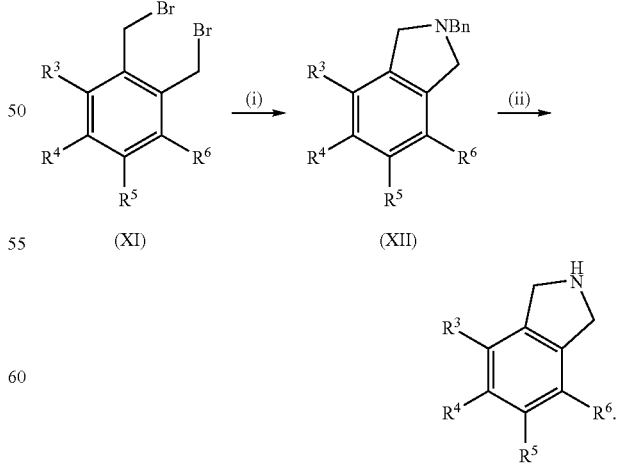

Scheme 3

Typical reaction conditions.
(i) Treatment of (XI) with benzylamine in a suitable solvent such as ethanol, chlorobenzene or toluene at room temperature or elevated temperatures.
(ii) Deprotection using a debenzylating agent such as a palladium catalyst and hydrogen in a suitable solvent at room temperature or α-chloroethyl chloroformate in a suitable solvent such as dichloromethane or methanol at elevated temperatures, followed by hydrolysis using a suitable hydroxide source such as lithium hydroxide in a suitable solvent such as methanol and tetrahydrofuran at room temperature.

Where $R^2$, $R^3$, $R^4$ and $R^5$ are not cyano, thio or amino, a lactam of formula (III) may be prepared from a compound of formula (XIII);

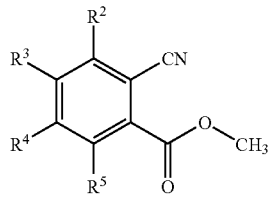

(XIII)

by treatment with a reducing agent such as sodium borohydride with cobalt chloride hexahydrate in an alcoholic solvent such as methanol at 0–25° C.

Where $R^2$, $R^3$, $R^4$ and $R^5$ are not thio, a lactam of formula (III) can be prepared from a compound of formula (XIV);

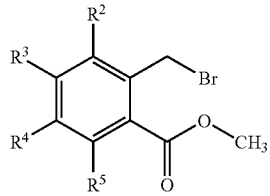

(XIV)

by lactam formation using a suitable ammonia source such as ammonium hydroxide in a suitable solvent such as tetrahydrofuran or ethanol at 0–25° C.

Where $R^2$, $R^3$, $R^4$ and $R^5$ are not thio or amino, a lactam of formula (III) can be prepared from a compound of formula (XV);

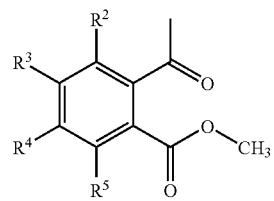

(XV)

by treatment of (XV) with a suitable hydroxylamine source such as hydroxylamine hydrochloride and base such as pyridine in a suitable solvent such as methanol or ethanol at elevated temperatures to form a benzo[d][1,2]oxain-1-one, followed by ring opening and lactam formation by treatment with a suitable reducing agent such as zinc in an acid such as glacial acetic acid or hydrochloric acid at elevated temperatures.

Referring to the general methods above, it will be readily understood to the skilled person that where protecting groups are present, these will be generally interchangeable with other protecting groups of a similar nature, e.g. where an amine is described as being protected with a tert-butoxycarbonyl group, this may be readily interchanged with any suitable amine protecting group.

It will be readily understood to the skilled person that particular steps in the general methods presented herein above may be suitably combined in any other manner not shown to provide a compound according to the present invention.

A pharmaceutically acceptable salt of a compound of the invention may be readily prepared by mixing together solutions of a compound of the invention and the desired acid or base, as appropriate. The salt may precipitate from solution and be collected by filtration or may be recovered by evaporation of the solvent.

Thus, in summary, the invention provides:
(i) a process for the preparation of a compound of formula (I) or a pharmaceutically acceptable salt, solvate, polymorph or pro-drug thereof;
(ii) a pharmaceutical composition including a compound of formula (I) or a pharmaceutically acceptable salt, solvate, polymorph or pro-drug thereof, together with a pharmaceutically acceptable excipient, diluent or carrier;
(iii) the use of a compound of formula (I) or of a pharmaceutically acceptable salt, solvate, polymorph, pro-drug or composition thereof, for the manufacture of a medicament for the treatment of any of the conditions mentioned herinbefore;
(iv) the use of a compound of formula (I) or of a pharmaceutically acceptable salt, solvate, polymorph, pro-drug or composition thereof, for the manufacture of a medicament for the treatment of any of the conditions mentioned herinbefore;
(v) a method of treatment of a mammal to treat any of the conditions mentioned herinbefore, including treating said mammal with an effective amount of a compound of formula (I) or with a pharmaceutically acceptable salt, solvate, polymorph, pro-drug or composition thereof;
(vi) a method for the treatment of any of the conditions mentioned herinbefore, which comprises administering to a patient in need of such treatment, either simultaneously, separately or sequentially, a combination of a compound of formula (I) and a further pain agent.
(vii) the use of a combination of a compound of formula (I) and a further therapeutic agent for the manufacture of a medicament for the treatment of any of the conditions mentioned herinbefore; and
(viii) a product containing a compound of formula (I) and a further therapeutic agent as a combined preparation for simultaneous, separate or sequential use in the treatment of any of the conditions mentioned herinbefore.

The present invention is illustrated by the following non-limiting examples and intermediates.

EXAMPLE 1

2-Aminomethyl-5-chloro-benzoic acid hydrochloride salt

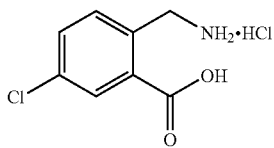

A mixture of 6-chloro-2,3-dihydro-isoindol-1-one (0.115 g, 0.68 mmol) and 6M hydrochloric acid (8 ml) in dioxan (1 ml) was heated to 110° C. for 18 hours. After cooling to room temperature the solid was filtered off and dried in vacuo to give the title compound (0.0055 g, 4%) as a beige solid.

$^1$H-NMR (400 MHz, DMSO): δ=4.30 (brs, 2H), 7.58 (dd, 1H), 7.76 (dd, 1H), 8.22 (brs, 3H). LRMS (Electrospray): m/z [MH$^+$]186. Microanalysis: Found: C, 43.13; H, 4.05; N, 6.18. C$_8$H$_8$NO$_2$Cl.HCl requires C, 43.26; H, 4.08; N, 6.31%.

EXAMPLE 2

2-Aminomethyl-4,5-dichloro-benzoic acid hydrochloride salt

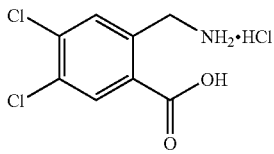

The above compound was synthesised (0.159 g, 46%) as a gold solid using a method similar to Example 1.

$^1$H-NMR (400 MHz, DMSO): δ=4.32 (s, 2H), 7.9 (s,1H), 8.12 (s,1H), 8.28 (brs, 3H). LRMS (Electrospray): m/z [M]$^+$220. Microanalysis: Found: C, 36.98; H, 3.06; N, 5.21. C$_8$H$_8$NO$_2$Cl.HCl.0.1H$_2$O requires C, 37.20; H, 3.20; N, 5.42%.

EXAMPLE 3

2-Aminomethyl-3-bromo-benzoic acid hydrochloride salt

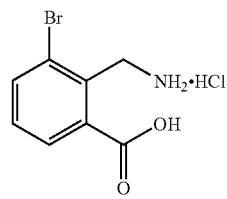

A mixture of 2-(tert-Butoxy carbonylamino-methyl)-3-bromo-benzoic acid (0.188 g, 0.57 mmol) in 2M HCl in diethyl ether (10 ml) was stirred at room temperature for 18 hours. The solvent was removed by evaporation under reduced pressure. The solid was diluted with ethyl acetate/dioxan (1:1) (10 ml) and stirred at room temperature for 1.5 hours. The solid was filtered off and dried to give the title compound (0.02 g, 13%) as a white solid.

$^1$H-NMR (400 MHz, DMSO): δ=4.40 (s, 2H), 7.44 (t, 1H), 8.0 (m, 2H), 8.1 (brs, 3H). LRMS (Electrospray): m/z [M]$^+$230. Microanalysis: Found: C, 35.09; H, 3.39; N, 5.12. C$_8$H$_8$NO$_2$Br. 1.2HCl requires C, 35.24; H, 3.41; N, 4.87%.

EXAMPLE 4

2-Aminomethyl-6-chloro-benzoic acid hydrochloride salt

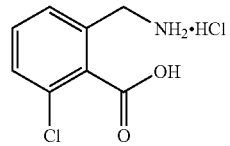

The above compound was synthesised (0.0051 g, 11%) as a white solid using a method similar to Example 3.

$^1$H-NMR (400 MHz, DMSO): δ=4.0 (s, 2H), 7.51 (m, 3H), 8.4 (brs, 3H). LRMS (Electrospray): m/z [M–H]$^+$184.

EXAMPLE 5

2-(1-Amino-ethyl)-benzoic acid hydrochlorid salt

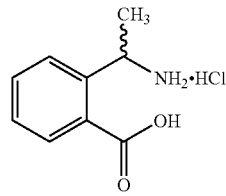

The above compound was synthesised (0.006 g, 8%) as a white solid using a method similar to Example 3.

$^1$H-NMR (400 MHz, DMSO): δ=1.58 (d, 3H), 5.22 (brs, 1H), 7.50 (t, 1H), 7.72 (t, 1H), 7.78 (d, 1H), 7.92 (d, 1H), 8.42 (brs, 3H). LRMS (Electrospray): m/z [M–H]$^+$166. Microanalysis: Found: C, 52.84; H, 5.98; N, 6.74. C$_9$H$_{11}$NO$_2$.HCl requires C, 52.65; H, 5.94; N, 6.82%.

EXAMPLE 6

2,3-Dihydro-1H-isoindole-4-carboxylic acid

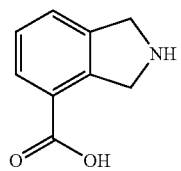

To a suspension of the 2,3-dihydro-1H-isoindole-4-carboxylic acid methyl ester hydrochloride salt (0.18 g, 0.83 mmol) in 25% MeOH/THF (4 ml) was added dropwise lithium hydroxide (0.08 g, 3.32 mmol) in water (1 ml), followed by addition of water (2 ml) and the clear solution stirred at room temperature under nitrogen for 5 h. The solution was acidified with aq. HCl. and purified by ion-exchange (DOWEX™ 50WX2-100) resin eluting with a solvent gradient of ammonia:water (5:95) to give the title compound (0.0059 g, 4%) as a white solid.

$^1$H-NMR (400 MHz, D$_2$O): δ=4.6 (s, 2H), 4.82 (s, 2H), 7.43 (m, 2H), 7.72 (d, 1H). LRMS (APCl): m/z [M+H]$^+$164.

EXAMPLE 7

3-(2-Aminomethyl-5-chloro-phenyl)-4-H-[1,2,4] loxadiazol-5-one hydrochloride salt

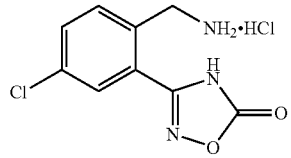

A mixture of [4-chloro-2-(5-oxo-4,5-dihyro-[1,2,4]oxa-diazolyl-3-yl]-di carbamic acid tert butyl ester (0.2875 g, 0.68 mmol) in 4M HCl in dioxan (8 ml) was stirred at 0° C. then warmed to room temperature for 18 hours under nitrogen. The solid was filtered off and washed with dichloromethane (5 ml) and diethyl ether (5 ml). The dark beige solid was taken into 6M hydrochloric acid and washed with dichloromethane (3×10 ml), and ethyl acetate (3×10 ml). The HCl solution was evaporated under reduced pressure and the resultant solid was dried under reduced pressure to give the title compound (0.028 g, 16%) as a beige solid.

$^1$H-NMR (400 MHz, CD$_3$OD): δ=4.41 (s, 2H), 7.68 (dd, 1H), 7.74 (dd, 1H), 7.82 (d, 1H). LRMS (APCl): m/z [M+H]$^+$226.

Preparation 1

2-chloro-6-amino-benzoic acid methyl ester[1]

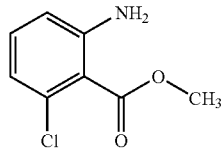

To 2-amino-6-chloro-benzoic acid (1 g, 5.83 mmol), and potassium carbonate (1.21 g, 8.74 mmol) in DMF (15 ml) was added dropwise methyl iodide (0.47 ml, 7.58 mmol) and the reaction mixture stirred at room temperature for 18 hours. The reaction mixture was quenched with water (150 ml). The aqueous layer was extracted with diethyl ether (3×50 ml), dried over magnesium sulphate. The mixture was filtered and the solvent removed by evaporation under reduced pressure to give an orange residue. The residue was dissolved in a minimum quantity of dichloromethane and purified by flash chromatography on silica gel eluting with a solvent gradient of heptane:ethyl acetate (3:1) to give the title compound (0.61 g, 56%) an orange oil.

$^1$H-NMR (400 MHz, CDCl$_3$): δ=3.92 (s, 3H), 4.8 (brs, 2H), 6.48 (dd, 1H), 6.72 (dd, 1H), 7.4 (m, 1H). LRMS (Electrospray): m/z [M+H+Na]$^+$208. Microanalysis: Found: C, 51.69; H, 4.34; N, 7.46. C$_8$H$_8$NO$_2$Cl. requires C, 51.77; H, 4.34; N, 7.55%.

Similarly prepared was;

Preparation 2

3-chloro-6-amino-benzoic acid methyl ester[2]

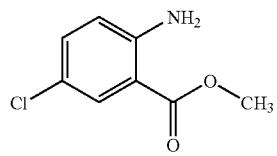

The above compound was synthesised (0.33 g, 15%) as a white solid.

$^1$H-NMR (400 MHz, CDCl$_3$): δ=3.89 (s, 3H), 5.65 (brs, 2H), 6.60 (dd, 1H), 7.20 (dd, 1H), 7.82 (m, 1H). LRMS (Electrospray): m/z [M–H]$^+$184. Microanalysis: Found: C, 51.84; H, 4.32; N, 7.49. C$_8$H$_8$NO$_2$Cl. Requires C, 51.77; H, 4.34; N, 7.55%.

1. Cai, Sui Xiong: Zhou, Zhang-Lin: Huang, Jin-Cheng; Whittermore, Edward R; Egbuwoku, Zizi O *J. Med, Chem.;* 39, 17, 1996, 3248–3455.
2. Commercially available from Sigma Aldrich.

Preparation 3

3-chloro-6-cyano-benzoic acid methyl ester

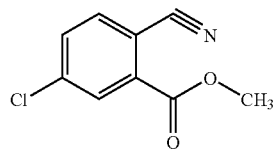

Water was added (5 ml) to a stirred suspension of 2-amino-5-chloro methyl benzoate (0.33 g, 1.77 mmol) in concentrated hydrochloric acid (1.1 ml) at 0° C. A solution of sodium nitrite (0.12 g, 1.77 mmol) in water (1 ml) was added dropwise and the solution stirred until complete dissolution. The diazonium salt was brought to Ph. 6.0. with saturated sodium bicarbonate. In a separate flask, a solution of CuSO$_4$.5H$_2$O (0.53 g, 2.12 mmol) in water (2 ml) was added dropwise to a stirred solution of potassium cyanide (0.53 g, 8.13 mmol) in water (2 ml) at 0° C. Toluene (3 ml) was added and the resultant brown mixture stirred and heated to 60° C.

The previously prepared diazonium solution was added to the Cu(I)CN at 60° C. over a period of 30 mins. The reaction mixture was heated to 70° C. for an additional 1 hour, then cooled to room temperature. The brown mixture was diluted with ethyl acetate (70 ml), filtered through a pad of celite™, washed with ethyl acetate (3×20 ml), the combined organics washed with brine (50 ml), dried over magnesium sulfate, filtered and the solvent removed by evaporation under reduced pressure to give a dark orange solid. The solid was dissolved in minimum dichloromethane was purified by flash chromatography on silica gel eluting with a solvent gradient of heptane: ethyl acetate (3:1) to give the title compound (0.23 g, 65%) as an off-white solid.

$^1$H-NMR (400 MHz, CDCl$_3$): δ=4.0 (s, 3H), 7.62 (dd, 1H), 7.72 (dd, 1H), 8.12 (d, 1H). LRMS (Electrospray): m/z [M+H]$^+$218. Microanalysis: Found: C, 55.16; H, 3.09; N, 7.08. C$_9$H$_6$NO$_2$Cl requires C, 55.26; H, 3.09; N, 7.16%.

Similarly prepared was;

Preparation 4

2–Chloro-6-cyano-benzoic acid methyl ester[3]

The above compound was synthesised (0.34 g, 64%) as a yellow solid.

$^1$H-NMR (400 MHz, CDCl$_3$): δ=4.02 (s, 3H), 7.50 (dd, 1H), 7.66 (m, 2H). LRMS (Electrospray): m/z [M+Na+H]$^+$ 218. Microanalysis: Found: C, 55.24; H, 3.07; N, 7.19. C$_9$H$_6$NO$_2$Cl requires C, 55.26; H, 3.09; N, 7.16%.

3. Patent; CIBA-GEIGY; DE 2525587; 1975; Chem. Abstr.; 84; 91648.

Preparation 5

6-Chloro-2,3-dihydro-isoindol-1-one[4]

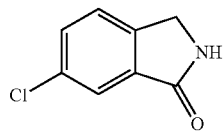

To a stirred solution of the 3-chloro-6-cyano-benzoic acid methyl ester (0.22 g, 1.12 mmol) and cobalt chloride hexahydrate (0.54 g, 2.24 mmol) in methanol (18 ml) was added sodium borohydride portionwise (CAUTIOUSLY as EXOTHERM). The black mixture was stirred at room temperature under nitrogen for 1 hour. The mixture was quenched with 5% HCl (aq. 10 ml), diluted with water (10 ml) and concentrated ammonium hydroxide (20 ml) and extracted with ethyl acetate (3×50 ml). The combined organics were dried over (MgSO$_4$), filtered and the solvent removed by evaporation under reduced pressure to give a brown solid. The solid was purified by flash chromatography on silica gel eluting with a solvent gradient of ethyl acetate to give the title compound (0.116 g, 61%) as a yellow solid.

$^1$H-NMR (400 MHz, CDCl$_3$): δ=4.42 (d, 2H), 6.6 (brs, 1 H), 7.4 (dd, 1H), 7.54 (dd, 1H), 7.84 (d, 1H). LRMS (Electrospray): m/z [M+H+Na]$^+$190.

Similarly prepared were;

Preparation 6

7-Chloro-2,3-dihydro-isoindol-1-one

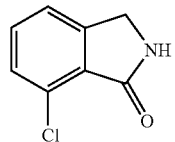

The above compound was synthesised (0.17 g, 62%) as a yellow solid using a method similar to Preparation 3.

$^1$H-NMR (400 MHz, CDCl$_3$): δ=4.41 (s, 2H), 7.08 (brs, 1H), 7.36 (dd, 1H), 7.4 (dd, 1H), 7.48 (dd, 1H). LRMS (Electrospray): m/z [M−H]$^+$166.

Preparation 7

5,6-Dichloro-2,3-dihydro-isoindol-1-one[5]

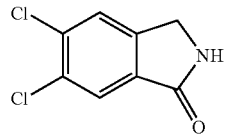

The above compound was synthesised (0.37 g, 25%) as an orange.

$^1$H-NMR (400 MHz, CDCl$_3$): δ=4.42 (s, 2H), 6.24 (brs, 1H), 7.6 (d, 1H), 7.86 (d, 1H). LRMS (Electrospray): m/z [M−2H]$^+$200.

4. Anderson, P. S. et. al. *J. Org. Chem;* 44, 9, 1979, 1519–1533.

5. Hennige, Hans; Kreher, Richard P.; Konrad, Michael; Jellito, Frank; *Chem Ber;* 121, 1988, 243–252.

Preparation 8

3-Bromide-2-bromomethyl-benzoic acid methyl ester[6]

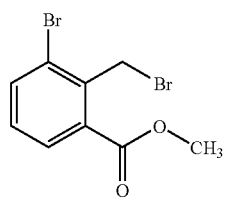

A mixture of 3-Bromo-2-methyl benzoic acid methyl ester (2.4 g, 10.29 mmol), NBS (1.83 g, 10.29 mmol) and AIBN (4 mg) in chlorobenzene (40 ml) was heated to 80° C. under nitrogen for 18 hours. The mixture was cooled in an ice-bath, filtered and the solvent removed by evaporation under reduced pressure. The orange residue was purified by flash chromatography on silica gel eluting with a solvent gradient of heptane:ethyl acetate (40:1) to give the title compound (2.74 g, 86%) as a colourless oil.

¹H-NMR (400 MHz, CDCl₃): δ=3.88 (s, 3H), 5.06 (s, 2H), 7.22 (dd, 1H), 7.68 (d, 1H), 7.89 (d, 1H). Microanalysis: Found: C, 35.21; H, 2.67; N, 0.00. C₉H₈Br₂O₂ requires C, 35.10; H, 2.62; N, 0.00%.
6. Tasaka, Akihiro; Kaku, Tomohiro; Kusaka, Masami; PCT Int. Appl (2001). WO 0120764

Preparation 9

4-Bromo-2,3-dihydro-isoindol-1-one⁷

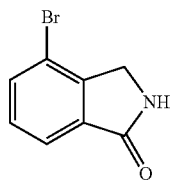

To a solution of the 3-bromo-2-bromomethyl-benzoic acid methyl ester (2.74 g, 8.88 mmol) in tetrahydrofuran (70 ml) at 0° C. was added 30% aq. ammonia (10 ml) and the mixture stirred at room temperature under nitrogen for 18 hours. The solvent was removed by evaporation under reduced pressure. The white residue was partitioned between ethyl acetate (50 ml) and 2M citric acid (50 ml). The ethyl acetate was dried magnesium sulfate, filtered and solvent removed by evaporation under reduced pressure. The orange oil was dissolved in minimum dichloromethane and purified by flash chromatography on silica gel eluting with a solvent gradient of dichoromethane/methanol (9:1) to give the title compound (1.5 g, 80%) as a white solid.

¹H-NMR (400 MHz, DMSO): δ=4.29 (s, 2H), 7.44 (t, 1H), 7.69 (d, 1H), 7.80 (d, 1H), 8.68 (brs, 1H). LRMS (Electrospray): m/z [M+2H]⁺214. Microanalysis: Found: C, 45.20; H, 2.90; N, 6.67. C₈H₆NOBr requires C, 45.31; H, 2.85; N, 6.60%.
7. Tasaka, Akihiro; Kaku, Tomohiro; Kusaka, Masami; PCT Int. Appl (2001). WO 0130764

Preparation 10

4-Bromo-1-oxo-1,3-dihydro-isoindole-2-carboxylic acid tert butyl ester

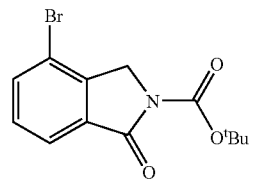

A mixture of the 4-bromo-2,3-dihydro-isoindol-1-one (0.159 g, 0.749 mmol), di tert butyl dicarbonate (0.33 g, 1.5 mmol), triethylamine (0.11 ml, 0.75 mmol) and DMAP (0.092 g, 0.75 mmol) in dichloromethane (7 ml) was stirred at room temperature under nitrogen for 18 hours. The yellow solution was purified by flash chromatography on silica gel eluting with a solvent gradient of heptane/ethyl acetate (3:1) to give the title compound (0.23 g, 99%) as a colourless residue.

¹H-NMR (400 MHz, CDCl₃): δ=1.6 (s, 9H), 4.64 (s, 2H), 7.4 (t, 1H), 7.74 (d, 1H), 7.84 (d, 1H). LRMS (Electrospray): m/z [M+2H+Na]⁺336. Microanalysis: Found: C, 50.45; H, 4.72; N, 4.38. C₁₃H₁₄NO₃Br requires C, 50.02; H, 4.52; N, 4.49%.

Similarly prepared were;

Preparation 11

7-Chloro-1-oxo-1,3-dihydro-isoindole-2-carboxylic acid tert butyl ester

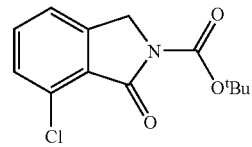

The above compound was synthesised (0.064 g, 80%) as a colourless foam.

¹H-NMR (400 MHz, CDCl₃): δ=1.62 (s, 9H), 4.65 (s, 2H), 7.34 (dd, 1H), 7.42 (dd, 1H), 7.52 (t, 1H). LRMS (Electrospray): m/z [M+Na]⁺289. Microanalysis: Found: C, 58.64; H, 5.43; N, 5.09. C₁₃H₁₄NO₃Cl requires C, 58.33; H, 5.27; N, 5.23%.

Preparation 12

1-Methyl-3-oxo-1,3-dihydro-isoindole-2-carboxylic acid tert butyl ester

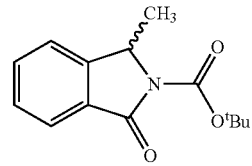

The above compound was synthesised (0.12 g, 72%) as a colourless oil from 3-methyl-2,3-dihydro-isoindol-1-one⁸ using a method similar to Preparation 6.

¹H-NMR (400 MHz, CDCl₃): δ=1.6 (brs, 12H), 5.06 (q, 1H), 7.44 (m, 2H), 7.64 (t, 1H), 7.89 (d, 1H). LRMS (Electrospray): m/z [M+Na]⁺269. Microanalysis: Found: C, 67.52; H, 6.93; N, 5.60. C₁₄H₁₇NO₃ requires C, 67.99; H, 6.93; N, 5.66%.
8. Kreher, Richard P,; Hennige, Hans; Konrad, Michael; Uhrig, Juergen; Clemens, Andrea; Z. Naturforsch. B; 46, 6, 1991, 809–828.

Preparation 13

2-(tert-Butoxy carbonylamino-methyl)-3-bromo-benzoic acid

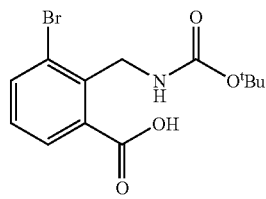

To a stirred solution of 4-bromo-1-oxo-1,3-dihydro-isoindole-2-carboxylic acid tert butyl ester (0.206 g, 0.66 mmol) in tetrahydrofuran (10 ml) was added dropwise a solution of aq. lithium hydroxide (1M, 2 ml, 1.98 mmol) and the mixture stirred at room temperature under nitrogen for 18 hours. The mixture was diluted with diethyl ether (30 ml) and washed with 1M HCl (10 ml). The aqueous layer was extracted with diethyl ether (2×20 ml) and the combined organics dried over magnesium sulfate, filtered and the solvent removed by evaporation under reduced pressure to give the title compound (0.188 g, 86%) as a white waxy solid.

LRMS (Electrospray): m/z [M+]330.

Similarly prepared were;

Preparation 14

2-(tert-Butoxy carbonylamino-methyl)-6-chloro-benzoic acid

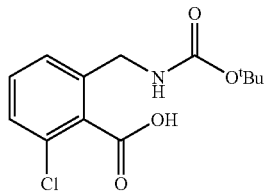

The above compound was synthesised (0.064 g, 94%) as a white solid.

$^1$H-NMR (400 MHz, CD$_3$OD): 67 =1.42 (s, 9H), 4.28 (s, 2H), 7.29–7.4 (m, 3H). LRMS (Electrospray): m/z [M–H]$^+$ 284. Microanalysis: Found: C, 54.51; H, 5.91; N, 4.54. C$_{13}$H$_{16}$NO$_4$Cl requires C, 54.65; H, 5.64; N, 4.90%.

Preparation 15

2-(tert-Butoxy carbonylamino-ethyl)-benzoic acid

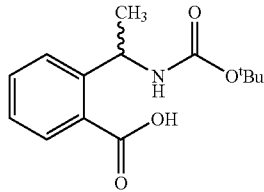

The above compound was synthesised (0.11 g, 86%) as a white solid.

$^1$H-NMR (400 MHz, CD$_3$OD): δ=1.40 (s, 12H), 5.5 (m, 1H), 7.3 (m, 1H), 7.51 (m, 2H), 7.89 (dd, 1H). LRMS (Electrospray): m/z [M–H]$^+$264.

Preparation 16

3-Hydroxyimino-indan-4-carboxylic acid

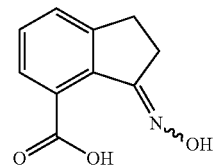

A mixture of the 3-oxo-indan-4-carboxylic acid[9] (1 g, 5.68 mmol), potassium carbonate (0.81 g, 5.85 mmol), hydroxylamine hydrochloride (0.39 g, 5.68 mmol) in methanol (25 ml) was stirred at room temperature under nitrogen for 18 hours. The solvent was removed by evaporation under reduced pressure and the residue taken into ethyl acetate (30 ml) and washed with water (30 ml). The aqueous layer was extracted with ethyl acetate (2×30 ml), the combined organics dried over magnesium sulfate, filtered, and the solvent removed by evaporation under reduced pressure to give the title compound (0.95 g, 87%) as a pale yellow solid.

$^1$H-NMR (400 MHz, CD$_3$OD): δ=3.04 (t, 2H), 3.19 (t, 2H), 7.54 (t, 1H), 7.64 (d, 1H), 8.2 (d, 1H). LRMS (APCl): m/z [M+H]$^+$192. Microanalysis: Found: C, 62.89; H, 4.71; N, 7.05. C$_{10}$H$_9$NO$_3$ requires C, 62.82; H, 4.74; N, 7.33%.

9. Panetta, Charles A; Dixit, Ajjit S; *Synthesis;* 1, 1981, 59–60.

Preparation 17

3-Amino-indan-4-carboxylic acid

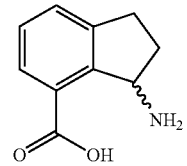

A mixture of the 3-hydroxyimino-indan-4-carboxylic acid (0.45 g, 2.35 mmol), zinc powder (0.72 g) in 1M HCl (10 ml) and glacial acetic acid (3 ml) was heated to 90° C. for 18 hours. The mixture was cooled to room temperature, the solid filtered off and the solvent removed by evaporation under reduced pressure. The residue was diluted with water (5 ml) and extracted with dichloromethane (3×10 ml) and ethyl acetate (5 ml). The aqueous fraction was purified by ion-exchange column (DOWEX™ 50WX2-100) eluting with a solvent gradient of ammonia: water (5:95) to give the title compound (0.142 g, 34%) as a white solid.

$^1$H-NMR (400 MHz, CD$_3$OD): δ=2.11 (m, 1H), 2.6 (m, 1H), 3.01 (m, 1H), 3.21 (m, 1H), 4.93 (m, 1H), 7.38 (d, 2H), 7.83 (m, 1H). LRMS (APCl): m/z [M–H]$^+$176. Microanalysis: Found: C, 64.81; H, 6.34; N, 7.53. C$_{10}$H$_{11}$NO$_2$. 0.15 NH$_4$Cl requires C, 64.85; H, 5.99; N, 7.56%.

Preparation 18

2-Benzyl-2,3-dihydro-1H-isoindole-4-carboxylic acid methyl ester

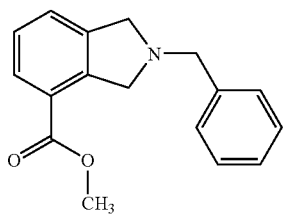

To a mixture of benzylamine (0.71 ml, 6.52 mmol), 10M NaOH, n-tetrabutyl ammonium chloride (0.12 g, 0.42 mmol) was added a solution of 2,3-bis-bromomethyl benzoic acid methyl ester[10] (1.20 g, 3.74 mmol) and the mixture stirred at room temperature under nitrogen for 18 hours. The mixture was poured into water (50 ml). The aqueous fraction was extracted with ethyl acetate (10 ml), the organics combined, washed with brine (10 ml), dried over magnesium sulfate, filtered and the solvent removed by evaporation under reduced pressure to give an orange oil. The oil was taken into minimum amount of dichloromethane and purified by flash chromatography on silica gel eluting with a solvent gradient of heptane:ethyl acetate (3:1) to give the title compound (0.57 g, 57%) as a pale yellow oil.

$^1$H-NMR (400 MHz, CDCl$_3$): δ=3.87 (s, 3H), 3.95 (s, 4H), 4.34 (s, 2H), 7.27 (m, 3H), 7.35 (m, 2H), 7.42 (m, 2H), 7.85 (d, 1H). LRMS (APCl): m/z [M+H]$^+$268. Microanalysis: Found: C, 75.83; H, 6.40; N, 5.20. C$_{17}$H$_{17}$NO$_2$. 0.1 H$_2$O requires C, 75.87; H, 6.37; N, 5.20%.

10. Neubeck, H. K. *Montash. Chem;* 127, 2, 1996, 201–217.

Preparation 19

2,3-Dihydro-1H-isoindole-4carboxylic acid methyl ester hydrochloride salt

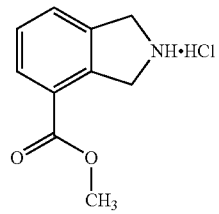

To a solution of 2-benzyl-2,3-dihydro-1H-isoindole-4-carboxylic acid methyl ester (0.3 g, 1.12 mmol) in dichloromethane (4 ml) at −10° C., was added dropwise α-chloroethyl chloroformate (0.16 ml, 1.46 mmol) and stirred at −10° C. for 30 mins. The solvent was removed by evaporation under reduced pressure and the residue dissolved in methanol (5 ml) and heated to 90° C. for 40 mins. The solution was cooled to room temperature and the solvent removed by evaporation under reduced pressure. The residue was diluted with ethyl acetate (30 ml), extracted into sat. NaOH solution to give a hygroscopic solid, used without further purification.

$^1$H-NMR (400 MHz, CD$_3$OD crude): δ=3.9 (s, 3H), 4.6 (brs, 2H), 4.92 (brs, 2H), 7.51 (d, 1H), 7.61 (d, 1H), 8.0 (d, 1H). LRMS (APCl): m/z [M+H]$^+$178.

Preparation 20

(4-Chloro-2-cyano-benzyl)-diocarbamic acid tert butyl ester

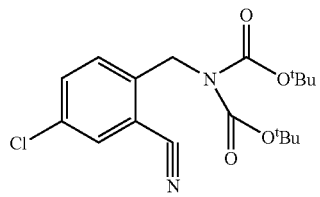

To a suspension of sodium hydride (1.91 g, 47.72 mmol) in anhydrous tetrahydrofuran (30 ml) at room temperature under nitrogen, was added a solution of 2-bromomethyl-5-chloro-benzonitrile[11] (10 g, 43.39 mmol) in anhydrous tetrahydrofuran (35 ml), followed by the dropwise addition of di-tert butyl imino dicarboxylate (10.37 g, 47.72 mmol) in anhydrous tetrahydrofuran (30 ml). The reaction mixture was stirred at room temperature for 28 hours under nitrogen. The reaction was quenched with water (50 ml) and the solvent removed under reduced pressure. The aqueous layer was extracted with diethyl ether (3×100 ml), the combined organics washed with brine (50 ml), dried with magnesium sulfate, filtered and the solvent removed by evaporation under reduced pressure. The residue was purified by flash chromatography on silica gel eluting with a solvent gradient of heptane:ethyl acetate (4:1) to give the title compound (13.45 g, 84%) as a pale yellow solid.

$^1$H-NMR (400 MHz, CDCl$_3$): δ=1.46 (s, 18H), 4.98 (s, 2H), 7.28 (d, 1H), 7.53 (d, 1H), 7.61 (d, 1H). LRMS (APCl): m/z [M+H]$^+$389. Microanalysis: Found: C, 59.37; H, 6.47; N, 7.09. C$_{18}$H$_{23}$N$_2$O$_4$Cl requires C, 58.93; H, 6.32; N, 7.64%.

11. Ando, Kazuo; Tokoroyama, Takshi; Kubota, Takishi; *Bull Chem. Soc. Jpn.,* 53, 10, 1980, 2885–2890.

Preparation 21

[4-chloro-2-(N-hydroxycarbamimidoyl)-benzyl]-diocarbamic acid tert butyl ester

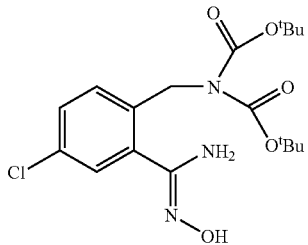

A mixture of hydroxylamine hydrochloride (1.33 g, 19.08 mmol) and triethylamine (2.9 ml, 20.99 mmol) was stirred at room temperature in absolute ethanol (200 ml) for 30 mins. To this was added (4-chloro-2-cyano-benzyl)di carbamic acid tert butyl ester (7 g, 19.08 mmol) and heated to 85° C. for 18 hours. The ethanol was removed by evaporation under reduced pressure then diluted with water (100 ml). The aqueous phase was extracted with ethyl acetate (3×75 ml), the combined organics dried over magnesium sulfate, filtered and the solvents removed by evaporation under reduced pressure to give a yellow residue. The residue was dissolved in minimum dichloromethane and purified on flash chromatography on silica gel eluting with a solvent gradient of heptane:ethyl acetate (4:1) to give the title compound (1.03 g, 13%) as a pale yellow foam.

$^1$H-NMR (400 MHz, CDCl$_3$): δ=1.45 (s, 18H), 4.84 (s, 2H), 5.70 (brs, 2H), 7.22 (d, 1H), 7.36 (m, 3H). LRMS (APCl): m/z [M−H]$^+$398. Microanalysis: Found: C, 54.26; H, 6.60; N, 10.20. C$_{18}$H$_{20}$N$_3$O$_5$Cl requires C, 54.07; H, 6.55; N, 10.51%.

Preparation 22

[4-Chloro-2-(5-oxo-4,5-dihyro-[1,2,4]oxadiazolyl-3-yl]-di-carbamic acid tert butyl ester

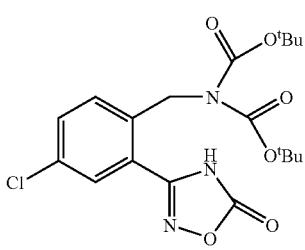

To a solution of [4-chloro-2-(N-hydroxycarbamimidoyl)-benzyl]-di carbamic acid tert butyl ester (0.85 g, 2.13 mmol) in anhydrous tetrahydrofuran (100 ml) was added carbonyl diimidazole (0.52 g, 3.19 mmol) and the mixture was stirred and heated to 90° C. for 18 hours under nitrogen. The mixture was cooled to room temperature and the solvent removed by evaporation under reduced pressure. The brown residue was dissolved in minimum dichloromethane and purified by flash chromatography eluting with a solvent gradient of heptane:ethyl acetate (4:1) to (1:1) to ethyl acetate to dichloromethane:methanol (9:1) to give the title compound (0.3105 g, 34%) as a brown glass solid.

$^1$H-NMR (400 MHz, CDCl$_3$): δ=1.50 (s, 18H), 4.75 (s, 2H), 7.52 (brs, 2H), 7.52 (brs, 2H), 7.64 (s, 1H). LRMS (APCl): m/z [M−H]$^+$424.

PHARMACEUTICAL COMPOSITION EXAMPLES

In the following Examples, the active compound can be any compound of formula (I) and/or a pharmaceutically acceptable salt, solvate, or physiologically functional derivative thereof.

(i) Tablet Compositions

The following compositions A and B can be prepared by wet granulation of ingredients (a) to (c) and (a) to (d) with a solution of povidone, followed by addition of the magnesium stearate and compression.

|  | mg/tablet | mg/tablet |
| --- | --- | --- |
| Composition A | | |
| (a) Active ingredient | 250 | 250 |
| (b) Lactose B.P. | 210 | 26 |
| (c) Sodium Starch Glycollate | 20 | 12 |
| (d) Povidone B.P. | 15 | 9 |
| (e) Magnesium Stearate | 5 | 3 |
|  | 500 | 300 |
| Composition B | | |
| (a) Active ingredient | 250 | 250 |
| (b) Lactose | 150 | 150 |
| (c) Avicel PH 101 | 60 | 26 |
| (d) Sodium Starch Glycollate | 20 | 12 |
| (e) Povidone B.P. | 15 | 9 |
| (f) Magnesium Stearate | 5 | 3 |
|  | 500 | 300 |

|  | mg/tablet | mg/tablet |
| --- | --- | --- |
| Composition C | | |
| Active ingredient | 100 | |
| Lactose | 200 | |
| Starch | 50 | |
| Povidone | 5 | |
| Magnesium Stearate | 4 | |
|  | 359 | |

The following compositions D and E can be prepared by direct compression of the admixed ingredients. The lactose used in formulation E is of the direct compression type.

|  | mg/tablet |
| --- | --- |
| Composition D | |
| Active ingredient | 250 |
| Magnesium Stearate | 4 |
| Pregelatinised Starch NF15 | 146 |
|  | 400 |
| Composition E | |
| Active ingredient | 250 |
| Magnesium Stearate | 5 |
| Lactose | 145 |
| Avicel | 100 |
|  | 500 |
| Composition F (Controlled release composition) | |
| (a) Active ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
|  | 700 |

The composition can be prepared by wet granulation of ingredients (a) to (c) with a solution of povidone, followed by addition of the magnesium stearate and compression.

Composition G (Enteric-Coated Tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-Coated Controlled Release Tablet)

Enteric-coated tablets of Composition F can be prepared by coating the tablets with 50 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

(ii) Capsule Compositions

Composition A

Capsules can be prepared by admixing the ingredients of Composition D above and filling two-part hard gelatin capsules with the resulting mixture. Composition B (infra) may be prepared in a similar manner.

|  | mg/capsule |
| --- | --- |
| Composition B | |
| (a) Active ingredient | 250 |
| (b) Lactose B.P. | 143 |
| (c) Sodium Starch Glycollate | 25 |
| (d) Magnesium Stearate | 2 |
| | 420 |
| Composition C | |
| (a) Active ingredient | 250 |
| (b) Macrogol 4000 BP | 350 |
| | 600 |

Capsules can be prepared by melting the Macrogol 4000 BP, dispersing the active ingredient in the melt and filling two-part hard gelatin capsules therewith.

| Composition D | |
| --- | --- |
| | mg/capsule |
| Active ingredient | 250 |
| Lecithin | 100 |
| Arachis Oil | 100 |
| | 450 |

Capsules can be prepared by dispersing the active ingredient in the lecithin and arachis oil and filling soft, elastic gelatin capsules with the dispersion.

| Composition E (Controlled release capsule) | |
| --- | --- |
| | mg/capsule |
| (a) Active ingredient | 250 |
| (b) Microcrystalline Cellulose | 125 |
| (c) Lactose BP | 125 |
| (d) Ethyl Cellulose | 13 |
| | 513 |

The controlled release capsule formulation can be prepared by extruding mixed ingredients (a) to (c) using an extruder, then spheronising and drying the extrudate. The dried pellets are coated with a release controlling membrane (d) and filled into two-part, hard gelatin capsules.

| Composition F (Enteric capsule) | |
| --- | --- |
| | mg/capsule |
| (a) Active ingredient | 250 |
| (b) Microcrystalline Cellulose | 125 |
| (c) Lactose BP | 125 |
| (d) Cellulose Acetate Phthalate | 50 |
| (e) Diethyl Phthalat | 5 |
| | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-Coated Controlled Release Capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) or a plasticizer to prevent membrane cracking during application or on storage. Suitable plasticizers include diethyl phthalate, tributyl citrate and triacetin.

| (iii) Intravenous injection composition | |
| --- | --- |
| Active ingredient | 0.200 g |
| Sterile, pyrogen-free phosphate buffer (pH 9.0) to | 10 ml |

The active ingredient is dissolved in most of the phosphate buffer at 35–40° C., then made up to volume and filtered through a sterile micropore filter into sterile 10 ml glass vials (Type 1) which are sealed with sterile closures and overseals.

| (iv) Intramuscular injection composition | |
| --- | --- |
| Active ingredient | 0.20 g |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

| (v) Syrup composition | |
| --- | --- |
| Active ingredient | 0.25 g |
| Sorbitol Solution | 1.50 g |

-continued

(v) Syrup composition

| | |
|---|---|
| Glycerol | 1.00 g |
| Sodium Benzoate | 0.005 g |
| Flavour | 0.0125 ml |
| Purified Water q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

(vi) Suppository composition

| | mg/suppository |
|---|---|
| Active ingredient | 250 |
| Hard Fat, BP (Witepsol H15 - Dynamit NoBel) | 1770 |
| | 2020 |

One-fifth of the Witepsol H15 is melted in a steam-jacketed pan at 45° C. maximum. The active ingredient is sifted through a 200 lm sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 lm stainless steel screen and, with continuous stirring, allowed to cool to 40° C. At a temperature of 38–40° C., 2.02 g aliquots of the mixture are filled into suitable plastic moulds and the suppositories allowed to cool to room temperature.

(vii) Pessary composition

| | mg/pessary |
|---|---|
| Active ingredient (63 lm) | 250 |
| Anhydrous Dextrose | 380 |
| Potato Starch | 363 |
| Magnesium Stearate | 7 |
| | 1000 |

The above ingredients are mixed directly and pessaries prepared by compression of the resulting mixture.

(viii) Transdermal composition

| | |
|---|---|
| Active ingredient | 200 mg |
| Alcohol USP | 0.1 ml |
| Hydroxyethyl cellulose | |

The active ingredient and alcohol USP are gelled with hydroxyethyl cellulose and packed in a transdermal device with a surface area of 10 cm².

Biological Data

Compounds of the invention were tested in the radioligand binding assay described within and were found to have binding affinities as follows;

| EXAMPLE | α2δ |
|---|---|
| 1 | 100 nM |
| 5 | 270 nM |
| 2 | 435 nM |
| 4 | 383 nM |
| 7 | 8 μM |

The invention claimed is:

1. A method of treating a disease selected from faintness attacks, hypokinesia, cranial disorders, neurodegenerative disorders, depression, anxiety, panic, neuropathic pain, sleep disorders and neuropathological disorders in a mammal, comprising administering to said mammal a compound or a pharmaceutically acceptable salt thereof of formula (I):

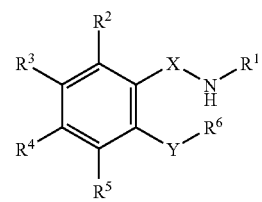

Formula (I)

wherein $R^1$ is H, $C_1$–$C_6$ alkyl or $C_3$–$C_8$ cycloalkyl;
X is —$(CH_2)_n$—$C(R^7)(R^8)$—;
Y is a direct link or —$(CH_2)_m$—$C(R^9)(R^{10})$—;
$R^7$, $R^8$, $R^9$ and $R^{10}$ are independently H or $C_1$–$C_6$ alkyl;
or $R^8$ and $R^1$ can be taken together with the nitrogen to which $R^1$ is attached to form a 4–8-membered heterocycloalkyl ring;
or $R^{10}$ and $R^1$ can be taken together with the nitrogen to which $R^1$ is attached to form a 4–8-membered heterocycloalkyl ring;
or $R^8$ and $R^{10}$ can be taken together with the carbons to which they are attached to form a 4–8-membered carbocyclic ring;
n is 0, 1 or 2;
m is 0, 1 or 2;
$R^2$, $R^3$, $R^4$ and $R^5$ are independently selected from H, $C_1$–$C_6$ alkyl, $C_1$–$C_6$ alkoxy, hydroxy, halogen, hydroxycarbonyl, $C_1$–$C_6$ alkoxycarbonyl, cyano, sulfonyl, $C_1$–$C_6$ alkylsulfonyl, thio, $C_1$–$C_6$ alkylthio, sulfonamide, perfluoro-$C_1$–$C_6$ alkyl, perfluoro-$C_1$–$C_6$ alkoxy, $C_3$–$C_8$ cycloalkyl, 4–8 membered heterocycloalkyl, amino, ($C_1$–$C_6$ alkyl or di-$C_1$–$C_6$ alkyl)amino, aminocarbonyl, ($C_1$–$C_6$ alkyl or di-$C_1$–$C_6$ alkyl)aminocarbonyl, $C_1$–$C_6$ acylamino, (N—$C_1$–$C_6$ alkyl)$C_1$–$C_6$ acylamino, phenyl or monocyclic heteroaryl, wherein phenyl and monocyclic heteroaryl are optionally substituted with $C_1$–$C_6$ alkyl, $C_1$–$C_6$ alkoxy, hydroxy, halogen, hydroxycarbonyl, $C_1$–$C_6$ alkoxycarbonyl or perfluoro-$C_1$–$C_6$ alkoxy;
or any one or two of $CR^2$, $CR^3$, $CR^4$ and $CR^5$ may be replaced with a nitrogen;
or $R^2$ and $R^3$ or $R^3$ and $R^4$ or $R^4$ and $R^5$ may be taken together with the carbons to which they are attached to form fused $C_5$–$C_8$ cycloalkyl, 4–8 membered heterocycloalkyl, phenyl or monocyclic heteroaryl;

or $R^1$ and $R^2$ can be taken together with the nitrogen to which $R^1$ is attached to form a 4–8-membered heterocycloalkyl ring;

or $R^8$ and $R^2$ can be taken together with the carbons to which they are attached to form a 4–8-membered carbocyclic or heterocycloalkyl ring; and $R^6$ is hydroxycarbonyl or a carboxylic acid biostere or a prodrug thereof.

2. A method according to claim 1, wherein the disease is neuropathic pain.

3. A method according to claim 1, wherein Y is a direct link.

4. A method according to claim 1, wherein $R^7$ is H and $R^8$ is H, methyl, or $R^8$ and $R^2$ are taken together with the carbons to which they are attached to form a 5-membered carbocyclic ring, or $R^8$ and $R^1$ are taken together with the nitrogen to which $R^1$ is attached to form a 5-membered heterocycloalkyl ring.

5. A method according to claim 1, wherein $R^2$, $R^3$, $R^4$ and $R^5$ are independently selected from H and halogen.

6. A method according to claim 1, wherein $R^6$ is hydroxycarbonyl, tetrazole or oxazolidinone.

7. A method of treating a disease selected from faintness attacks, hypokinesia, cranial disorders, neurodegenerative disorders, depression, anxiety, panic, neuropathic pain, sleep disorders and neuropathological disorders in a mammal, comprising administering to said mammal a compound or pharmaceutically acceptable salt thereof of formula (II):

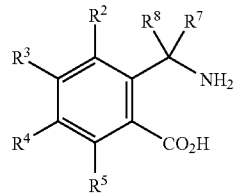

Formula (II)

wherein $R^7$ and $R^8$ are independently H or $C_1$–$C_6$ alkyl; and $R^2$, $R^3$, $R^4$ and $R^5$ are independently selected from H, $C_1$–$C_6$ alkyl, $C_1$–$C_6$ alkoxy, hydroxy, halogen, hydroxycarbonyl, $C_1$–$C_6$ alkoxycarbonyl, cyano, $C_1$–$C_6$ alkylsulfonyl, perfluoro-$C_1$–$C_6$ alkyl, perfluoro-$C_1$–$C_6$ alkoxy, $C_3$–$C_8$ cycloalkyl and 4–8 membered heterocycloalkyl;

or $R^8$ and $R^2$ can be taken together with the carbons to which they are attached to form a 4–8-membered carbocyclic or heterocycloalkyl ring.

8. A method according to claim 1, wherein the compound is selected from the group consisting of:
2-aminomethyl-5-chloro-benzoic acid;
2-aminomethyl-4,5-dichloro-benzoic acid;
2-aminomethyl-3-bromo-benzoic acid;
2-aminomethyl-6-chloro-benzoic acid;
2-(1-aminoethyl)-benzoic acid;
2,3-dihydro-1H-isoindole-4-carboxylic acid; and
3-(2-aminomethyl-5-chloro-phenyl)-4H-[1,2,4]oxadiazol-5-one;

or a pharmaceutically acceptable salt thereof.

* * * * *